(12) United States Patent
Sequeda Osorio et al.

(10) Patent No.: US 10,119,189 B2
(45) Date of Patent: Nov. 6, 2018

(54) BIOCOMPATIBLE MULTILAYER-THIN-FILM-TYPE COATING AS A SURFACE TREATMENT FOR BIOMEDICAL SUBSTRATES, AND METHOD FOR THE PRODUCTION THEREOF

(71) Applicant: UNIVERSIDAD DEL VALLE, Santiago de Cali (CO)

(72) Inventors: Federico Sequeda Osorio, Santiago de Cali (CO); Jose Oscar Gutierrez Montes, Santiago de Cali (CO); Alexander Ruden Muñoz, Santiago de Cali (CO)

(73) Assignee: Universidad del Valle, Santiago de Cali (CO)

( * ) Notice: Subject to any disclaimer, the term of this patent is extended or adjusted under 35 U.S.C. 154(b) by 288 days.

(21) Appl. No.: 14/896,384

(22) PCT Filed: Oct. 4, 2013

(86) PCT No.: PCT/IB2013/059109
§ 371 (c)(1),
(2) Date: Dec. 5, 2015

(87) PCT Pub. No.: WO2014/195768
PCT Pub. Date: Dec. 11, 2014

(65) Prior Publication Data
US 2016/0122865 A1 May 5, 2016

(30) Foreign Application Priority Data

Jun. 7, 2013 (CO) .................................. 13-138093

(51) Int. Cl.
C23C 14/34 (2006.01)
C23C 14/14 (2006.01)
C23C 28/00 (2006.01)
A61L 27/30 (2006.01)
A61L 31/08 (2006.01)
A61F 2/00 (2006.01)
C23C 14/06 (2006.01)
C23C 14/16 (2006.01)
C23C 14/35 (2006.01)

(52) U.S. Cl.
CPC ........ *C23C 14/3464* (2013.01); *A61F 2/0077* (2013.01); *A61L 27/30* (2013.01); *A61L 31/082* (2013.01); *C23C 14/0641* (2013.01); *C23C 14/14* (2013.01); *C23C 14/165* (2013.01); *C23C 14/34* (2013.01); *C23C 14/35* (2013.01); *C23C 28/321* (2013.01); *C23C 28/34* (2013.01); *A61L 2420/08* (2013.01)

(58) Field of Classification Search
CPC ...... C23C 14/0641; C23C 14/14; C23C 14/34
See application file for complete search history.

(56) References Cited

U.S. PATENT DOCUMENTS

| 5,234,561 A * | 8/1993 | Randhawa ............ C23C 14/325 204/192.12 |
| 8,003,232 B2 * | 8/2011 | Johansson ............ C23C 14/0641 428/216 |
| 9,388,487 B2 * | 7/2016 | Andersson .......... C23C 14/0641 |
| 2003/0113557 A1 * | 6/2003 | Chen ................. C04B 35/58007 428/457 |

OTHER PUBLICATIONS

Hernandez, Informador Tecnico, vol. 74, p. 39-43 (2010) (Year: 2010).*
Kelly, Vacuum 56 (2000) p. 159-172 (Year: 2000).*

* cited by examiner

*Primary Examiner* — Robert C Boyle
(74) *Attorney, Agent, or Firm* — Joseph L. Morales; The Morales Law Firm

(57) ABSTRACT

The present invention discloses a process for the manufacture of a thin-film multilayered coating used in treating biomedical substrates and a coating in multilayered thin-film form (S/TiN/Ti/TiZr) to treat biomedical substrates used in surgical implants.

3 Claims, 1 Drawing Sheet

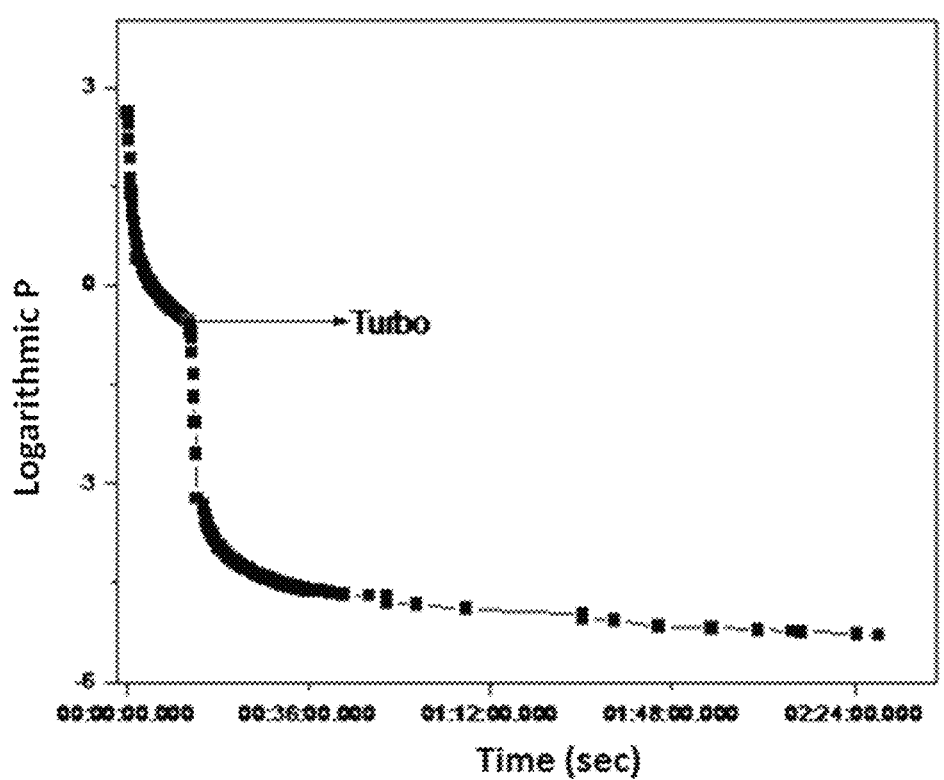

BIOCOMPATIBLE MULTILAYER-THIN-FILM-TYPE COATING AS A SURFACE TREATMENT FOR BIOMEDICAL SUBSTRATES, AND METHOD FOR THE PRODUCTION THEREOF

FIELD OF THE INVENTION

The invention is related to the field of biomaterials, specifically, it discloses a process for the manufacture of a thin-film multilayered coating used in treating biomedical substrates and a coating in multilayered thin-film form (S/TiN/Ti/TiZr) to treat biomedical substrates used in surgical implants.

BACKGROUND OF THE INVENTION

The field of biomaterials has become an area of vital importance because these materials increase the quality and longevity of human life and the science and technology associated with this field has led to the generation of a billion-dollar business. Biomaterials are polymers, metals, ceramics, inorganic materials, and synthetic and natural macromolecules (biopolymers), which are manufactured or processed to be used within or as medical devices or prostheses. These materials typically come into contact with cells, proteins, tissues, organs, and organic systems. The shape of the material and how it interacts with the environment (in blood contact for example) and its time of use will determine the properties required, suitable for a specific application.

A biomaterial must have as fundamental properties: a) good mechanical properties like hardness, tensile strength, modulus and elongation, from which its specific application is established; b) biocompatible, that is, it must be of low toxicity and not generate inflammatory or allergic reactions in the host, hence, the two relevant factors that influence a material's biocompatibility are the host response and the material degradation in physical environments; c) high corrosion and wear resistance understood as low wear and corrosion resistance of the implants in bodily fluids, given that wear results in the release of incompatible metal ions that cause allergic and toxic reactions in the host; d) osseointegration, that is, the incapacity of a surface on an implant of integrating with the adjacent bone and other tissues due to micro-movements, which result in loss of the implant. Thereby, materials with a suitable surface are essential in the integration process of an implant with the bone or the surrounding tissue. Surface chemistry, roughness, and topography play a dominant role in the development of good osseointegration.

Materials currently used for surgical implants include 316L stainless steel (316L SS), cobalt-chromium alloys (Co—Cr), and titanium alloys (Ti). Elements like nickel (Ni), chromium (Cr), and Co can be released from steel and from Co—Cr alloys due to corrosion in the physical environment. The toxic effects of metals (Ni, Cr, Co) released from prostheses implants have been studied and dermatitis has been reported due to the toxicity of the Ni element and numerous "in-vivo" studies in animals have shown carcinogenicity due to the presence of Co. These materials (316L SS and Co—Cr alloys) have a higher modulus of elasticity than that of bone (30-40 GPa), which causes insufficient capacity to transfer stress, resulting in bone resorption and weakening of the implant after some years of implantation. Commercially, pure Ti and the Ti-6Al-4V ELI alloy (Ti64-Extra Low Interstitial) are the most commonly used materials for applications in implants with low modulus of elasticity values that vary from 110 to 55 GPa compared to 316L SS (210 GPa) and Co—Cr alloys (240 GPa). Although titanium and its alloys, especially Ti64, have excellent corrosion resistance and are biocompatible, their long-term performance has raised concern due to the release of aluminum (Al) and vanadium (V) ions, which have been associated with health problems like Alzheimer's disease, neuropathy, and bone diseases like osteomalacia. Besides, V is toxic in its elemental form, as well as in oxide ($V_2O_5$) form, present on the surface. Titanium has low resistance to cutting, which makes it less applicable to the manufacture of screws for bones, plates to join bones, and similar applications. Finally, titanium and its alloys show severe wear when in contact with other metals, in addition to having a high friction coefficient, which leads to the formation of wear particles (debris), resulting in inflammatory reactions causing pain and softening of implants due to osteolysis. Given the limitations mentioned, the service period of implants manufactured with these materials is restricted to 10-15 years. This has stimulated research on developing new materials and processes to modify these surfaces.

To modify the surface of a substrate of biomedical application, the physical properties of the base material must be taken into account in order for the PVD-sputtering process to be highly reproducible, so that the surface properties of the protective coating are those sought for the biological application required. Properties like: roughness, friction, wear, hardness, modulus of elasticity, chemical inertness, corrosion resistance, and biocompatibility are essential when generating thin layers of nitrides, carbides, and oxides as protective systems of biocompatible substrates.

Keeping these facts in mind, there is a wide range of materials that fulfill this function, given their tribological or mechanical properties, in a way that positive response is integrally shown between the material to be implanted and the tissue that will host it. An example of this are urinary catheters, which, with the tissue, form incrustation-type bio-coatings where high bacterial proliferation exists, generating physiological complications; this can be avoided, as shown by research conducted by N. Laube, using a surface treatment with diamond-like carbon (DLC) [1,2]. Urinary catheters are not the only ones with this type of problem, devices like heart valves, coronary stents, and capillary tubes may generate hemostasis, produced by direct contact between the biomaterial and blood flow, where protein absorption takes place, leading to the adhesion and activation of platelets [3]; the blood flowing produces a shear effect on the surface of the biomaterial, affecting the tissue-coating system; these are some examples where the surface modification, whether through diminished friction coefficient, surface roughness, or chemical inertness may solve drawbacks.

Studies carried out by E. De Las Heras and F. Walthera [4] show that the type of surface treatment must be chosen adequately. One of the most currently used treatments is the nitriding procedure; nitriding 316L steel through plasma-assisted techniques results in increased surface hardness accompanied by diminished anticorrosion properties; nitriding extended austenitic phases in the protection process are generated accompanied by nitrides $Cr_2N$ and $Fe_4N$ [5], which correspond to a special triclinic arrangement [6]. To avoid these adverse biological effects, metallic and ceramic materials are used, which can be used as surface treatment to improve mechanical, tribological, anticorrosion, and biological properties. Among the metallic materials, there are Ti and zirconium (Zr) and ceramics like the nitrides of some transition metals (TiN, ZrN), carbides (TiC, SiC), oxides like $TiO_2$, $Al_2O_3$, and $ZrO_2$ and diamond-like carbon (DLC); these synthesized materials are employed as surface treatment using the PVD-sputtering technique [7, 8, 9, 10] and, normally have a thickness in the order of one to two micrometers. Multilayers have been used with good results since the 1970s, achieving better properties when compared to monolayers; the multilayered structure acts as a cracking inhibitor and, consequently, the coating's fracture toughness increases; multilayers normally use binary compounds, for example, TiN/TiC, TiN/ZrN and some have used their generic materials like: W/WC, Ti/TiN, c-BN/TiN [11, 12, 13, 14]. Multilayered coatings also have high hardness and excellent corrosion resistance.

When seeking to implant an inorganic biomaterial, such inorganic biomaterial has an effect on cellular action, which recognizes environmental signals that alter its phenotype. The specific properties that stimulate cell action on the surface take place due to four types of surface-tissue interactions:

Topography: directly implies cellular and molecular adherence on the surface; surface roughness, variable to discern when studying cell fixation.

Surface energy: it has been demonstrated that the preferential crystallographic orientation of the protective coating also plays a preponderant role in cell activity as far as its organization and fixation; these facts have been reported by Chiung-Fang Huang and Faghihi for osteoblastic cells in $Ti_6Al_4N$ alloys, in (100) and (110) directions, which reflects positive changes in biocompatibility [15, 16].

Self-diffusion of metallic cations: corrosion system, through high porosity and generation of mechanical wear problems producing particles. Many metals in pure state cause biocompatibility problems, for example: Ni (carcinogenic), 316L (release of Fe), Co, Cu, and V (highly toxic) [17, 18], hence, needing surface treatments, or passivation, to regulate the problem of anti-biocompatibility, bearing in mind that said treatments produce biocompatible materials soon after the implant; to cite some: TiAIV, Co—Cr—Mo, and Ti—Ni.

Tribological problems: metal ions and atomic groups or particles generated by wear processes cause adverse effects, which stimulates macrophages and T lymphocytes, which leads to cytokine production [19] that causes acute or chronic inflammation if the injurious agent persists [20].

From the aforementioned, two problems have been established around including thin layers as surface treatment: adherence and porosity. Coatings like Ti and Zr are part of the so-called transition metals [21, 22], which through reactive nitrogen gas sputtering form ZrN and TiN, which have similar physical and chemical characteristics, making them candidates as biocompatible material. Many studies have been conducted on surface modification based on these nitrides, for example, Hontsu et al. [23] demonstrated the pertinence of generating a TiN surface treatment for AISI 317L steel substrates and dope it with silver (Ag) particles provoking an antibacterial surface treatment.

One of the problems presented by 317L stainless steel is that it does not fulfill antibacterial functions, but when doped with Ag it acquires diminished anticorrosion properties; applying TiN coatings enables synergy with Ag ions [23]. Other thin-layered coatings exist, in ternary form like titanium aluminum nitride (TiAlN) or TiN/TiAlN multilayers, which are also part of the possible surface treatments of biocompatible substrates. Professor Braic from the Institute for Chemical-Pharmaceutical Research and Development in Romania [24] studied the corrosion and biocompatibility of TiN and TiAlN monolayers, in addition to (TiN/TiAlN)n multilayered coatings, with n number of bilayers, all using continuous arc PVD techniques, comparing the corrosion levels with respect to an alloy that is currently highly used for hip implants, Co—Cr—Mo. Regarding its biocompatibility results, the best viability was found for TiAlN coatings, followed by (TiN/TiAlN)720 and TiN. As a result of the biological tests, all the coatings studied showed good biocompatibility, without sign of cytotoxicity [24]. One of the surface treatments used most frequently are the nanometric layers of DLC or amorphous carbon (a-C); chemically, when atoms are not in their graphitic or diamond-like phase, their bond form is sp1 type (two valence electrons forming σbonds and the others in py and pz orbitals, forming πbonds), sp2 or sp3, the material obtained has different properties [25]. In DLC structures, bonds are normally sp2 and sp3 type, in different concentrations with hardness in the order of 30 GPa, transparent and with high wear resistance [26], making it a high-performance material, besides being biocompatible, by being chemically inert. Another carbon-based coating is the amorphous carbon nitride ($a-CN_x$), used for cutting and machining tools and because of its biological inertness as biomaterial, besides having excellent antiwear properties and low friction coefficient. This material is normally synthesized via PVD RF sputtering, through reactive methods, with $CH_4$, $N_2$, and argon [7].

In patents literature, reports are found for materials used as coating in multilayers. The closest anticipations to the invention correspond to some documents divulged on the state-of-the-art, like patent EP0366289 (MIDWEST RESEARCH TECHNOLOGIES), which shows as modalities of the invention multiple alternating layers of: (1) metal (Ti, Zr, Hf, Ta) and ceramic material (a metal nitride), (2) metal (Al, Si, Ti, Cr, Mg, Fe, Zr, Mo, W, Ta) and ceramic material (a metal oxide), (3) metal (Ti, Zr, Hf, Fe, or Ta), and ceramic material (a metal carbide), where each of the layers has a thickness of 0.1 to 5 µm and the substrate is a metal with a 2-µm thickness.

Patent request WO2007136777 shows a coating for an electricity conducting substrate made up of a metallic layer (Ti, Cr, Va, Al, Mo, Nb, W, Hf, Zi or alloys of such) followed by a ceramic layer (nitrides, carbides, oxides, oxicarbides, oxinitrides, borides, carboborides, borocarbonitrides, and combinations), and a diamond-like amorphous matrix (C, Si, N, H, O or transition metals) with a friction coefficient below 0.3, where the metallic and ceramic layer present a thickness of 0.01-30 µm and the amorphous matrix a thickness between 0.01 and 30 µm.

Patent request WO2010086598 divulges a coating for a substrate that comprises a layer of Ti, Cr, or an alloy of such, a metallic layer (NiTi, Ni, Ti, Cr, Al, Pt, Hf, Zr, Co, Cu, or Y) and a ceramic layer (Al or Si or a combination of nitrides, carbides, oxides, or borides of metals from groups 4, 5, or 6), which includes at least four layers of metal and ceramic material, where the coating has a thickness between 0.1 and 5 µm.

U.S. Pat. No. 4,904,542 shows a multilayer-type coating resistant to form a metallic substrate that comprises a metallic layer (Ti, Hf, Zr, Ta), a ceramic layer (metal nitride) that includes at least four metal and ceramic layers with thickness between 0.1 and 5 µm, preferably a 2-µm metallic layer and the ceramic layer with thickness of 0.5 µm. Likewise, it divulges an additional modality that comprises a metallic layer (Al, Si, Ti, Cr, Mg, Fe, Zr, Mo, W, Ta) and a ceramic material selected from a metal oxide (Al, Si, Ti, Cr, Mg, Fe, Zr, Mo, W, Ta). Another modality specifies a multilayer coating made up of a metallic layer (Ti, Hf, Zr, Fe, Ta) and a layer of ceramic material selected from a metal carbide (Ti, Hf, Zr, Fe, Ta).

In spite of the different materials existing in the state of the technique, there is need for a coating with improved mechanical and biological properties for substrates used in surgical implants (316L SS, Co—Cr alloy, Ti alloy—like Ti 64 and/or other materials). The coating of the invention solves the shortcomings of existing materials by disclosing a multilayered thin-film coating (S/TiN/Ti/TiZr) for substrates used in surgical materials that offers corrosion and wear resistance of said material with low genotoxicity, cytotoxicity and without effects in osseointegration.

OBJECTS OF THE INVENTION

In a first aspect, the invention provides a process to manufacture a thin-film multilayered coating for treatment of biomedical substrates.

In a second aspect, the invention provides a coating in multilayered thin-film form (S/TiN/Ti/TiZr) to treat biomedical substrates.

DETAILED DESCRIPTION OF THE INVENTION

In a first aspect, the invention reveals a process to manufacture a thin-film multilayered coating for treatment of biomedical substrates used in surgical implants, such as but not limited to 316L stainless steel SS, Co—Cr alloy, Ti alloy—like Ti 64 among other materials, which comprises:
a) Polishing the substrate surface to a granulometry of between 700 and 2500 to generate a mirror surface finish
b) Washing with acetone in ultrasound for 10 to 20 min
c) Submerging the substrate from stage b) into a PVD-DC magnetron sputtering reactor at a temperature between 20 and 25° C., vacuum of $5.1 \times 10^{-6}$ torr, and 50 to 60% relative humidity
d) Depositing the TiN coating layer with thickness between 550 and 590 nm from a Ti precursor target (99.99%) at a pressure from 2 to 4 mtorr, argon flow between 8 and 12 sccm, nitrogen flow between 0.1 and 0.2 sccm, precursor target power between 80 and 120 W, polarization voltage from −50 to −120 V, and interelectrode distance between 8 and 12 cm.
e) Depositing the Ti coating layer with thickness between 550 and 590 nm from a Ti precursor target (99.99%) at a pressure from 2 to 4 mtorr, argon flow between 8 and 12 sccm, precursor target potential between 80 and 120 W, polarization voltage from −50 to −120 V, and interelectrode distance between 8 and 12 cm.
f) Depositing the TiZr coating layer with thickness between 550 and 590 nm from a TiZr precursor target (30-70%) at a pressure from 2 to 4 mtorr, argon flow between 8 and 12 sccm, precursor target potential between 60 and 100 W, polarization voltage from −50 to −120 V, and interelectrode distance between 8 and 12 cm.

In a second aspect, the invention provides a coating in multilayered thin-film form (S/TiN/Ti/TiZr) for a substrate used in surgical materials obtained through the procedure already described, which comprises a TiN coating layer with thickness between 550 and 590 nm directly over the substrate, an intermediate Ti coating layer with thickness between 550 and 590 nm, and an external TiZr layer with thickness between 550 and 590 nm.

This thin-film multilayered coating (S/TiN/Ti/TiZr) has all the mechanical properties (high corrosion and wear resistance) and biocompatibility (high proliferation of cells, low genotoxicity and cytotoxicity, and high osseointegration) required for biomedical applications requiring high growth and cellular proliferation, as shown in the following examples.

The following examples are presented for the purpose of describing the preferred aspects of the invention, but do not constitute a limitation to its scope.

EXAMPLE 1

A bar of commercial grade biocompatible 316L Steel, 1.25 cm in diameter, was used as substrate. It was fractioned into cylinders 4 mm thick and their surface was polished by using silicon carbide sandpaper with granulometry between 700 and 2500 to generate a mirror surface finish. Prior to being submerged in the PVD-sputtering reactor, the cylinders were subjected to ultrasound washes for 15 min in acetone fluid, eliminating foreign agents like grease and dust, contamination due to manipulation. For synthesis of thin-film coatings from different materials (Ti, TiN,Ti/TiN, TiZr, TiZr/Ti/TiN), a DC magnetron sputtering system was used, consisting of a multisource PVD magnetron sputtering system (AJA ATC1500 INTERNATIONAL) with deposition reactor (15" internal diameter and 17" height), vacuum system and valves, and substrate holder.

Said system is housed in a class 1000 clean room for the areas where the coatings are deposited and class 10,000 for the room in general; this means that there are 1000 and 10,000 particles per cubic foot of air in these zones, respectively; the clean room is evaluated and certified by ISO 9001 standard C4—Contamination Control.

Conditions were adjusted to prepare the magnetron sputtering system to produce coatings, such as: clean room temperature at 22 ° C., relative humidity 55%, and initial atmospheric pressure of 762 torr.

FIG. 1 shows the logarithmic pressure (log P) ratio versus time of particle evacuation from the reactor, defining a base vacuum value of $5.1 \times 10^{-6}$ torr as sufficient condition for the synthesis process of the materials, taking an approximate time value of 2 h 30 min minimum to reach the base pressure and deposit the coatings.

For the synthesis of the different protective layers on the biocompatible 316L steel substrate, high-purity Ti and TiZr precursor targets were used. For all the coatings deposited, polarization voltage at −100V, base pressure of $5.1 \times 10^{-6}$ mtorr, and 10-cm interelectrode distance were established as fixed variables in the process. The synthesis conditions of each of the coating layers with 570-nm thickness (measured via profilometry) are presented in Table 1.

TABLE 1

Synthesis conditions of Ti, TiN, Ti/TiN, TiZr, and TiZr/Ti/TiN thin layer materials

| Material | Precursor target | Working pressure (mtorr) | Ar flow (sccm) | $N_2$ flow (Sccm) | Target power (W) |
|---|---|---|---|---|---|
| Ti | Ti (99.99%) | 3 | 10 | — | 100 |
| TiZr | TiZr (30%70%) | 3 | 10 | — | 80 |
| TIN | Ti (99.99%) | 3 | 10 | 0.15 | 100 |

EXAMPLE 2

The following presents the comparison of the analysis of surface, mechanical, tribological, and corrosion properties of the TiN/Ti/TiZr multilayer coating of the invention compared to Ti, TiN/Ti, TiZr, and TiN thin protective layers.

Analysis of Mechanical Properties

Hardness and modulus of elasticity measurements were made by using a nanoindenter (NANOVEA module IBIS—Technology), using the traditional Oliver and Pharr method, to fit the discharge curve. Nanoindentations were carried out in the following ranges: low (L), medium (M), and high (H) loads (L: 0.01-0.4 mN; M: 0.41-1 mN, and H: 1.1-10 mN) obtaining hardness and modulus of elasticity profiles in function of depth, determining a 1-mN ideal load that covers 10% of the thickness for the coatings. Nanoindentation tests were conducted by using a Berkovich pyramidal indenter coupled to the "IBIS" nanoindentation head by Fischer-Cripps Labs and a displacement control frame with compliance of 0.00035 um/mN, IBIS SOFWARE was used to control indentation, correction, and analysis of results. Hardness and modulus of elasticity were calculated recurring to the Oliver and Pharr model.

Analysis of Surface and Tribological Properties

To study the friction coefficient and wear of the coatings, a ball-on-disk system (CSEM—Tribometer) was used. The experimental conditions to measure the tribological properties were constant for the set of thin layers studied; the experimental conditions are shown in Table 2.

TABLE 2

Experimental conditions for the analysis of tribological properties

| | |
|---|---|
| Spherical counterpart | Alumina ($Al_2O_3$) |
| Diameter of the Spherical counterpart | 6 mm |
| Normal applied load | 1N |
| Run distance | 15 m |
| Test rate | 10 m/s |
| Test radius | 3 mm |
| Frequency of data recording | 2 Hz |

The friction coefficient analysis had statistical software support equipment (CSEM—tribotest, XTribo 2.5) and the ORIGIN mathematical package. To calculate thickness, roughness, and wear, a profilometer (XP—2 AMBIOS) was used. The rate of wear measurement was made by using the transversal area of the wear track after the BOD test and the Archard model, which proposes that the wear coefficient is directly proportional to the volume worn and inversely proportional to the normal load applied and the glide path.

Adherence Analysis

The scratch test was performed with Micro Test equipment, using a Rockwell C-type indenter with 200 μm radius, variable load from 0 to 100 N, rate of load application: 1 N/s, distance: 6 mm, and displacement rate: 4.5 mm/min.

Stereoscopy

Stereoscopies were taken by using Olympus SZ4045 equipment (reference #OCS07) to determine form of wear and cellular morphology, facilitating the calculation of cellular density per square micrometer.

Scanning Electron Microscopy and Energy Dispersive Spectroscopy (SEM/EDS)

For surface morphology description and cellular observation, SEM equipment was used (JEOL series JSM-6460) with EDS probe (model Oxford INCA—Energy EDS system), with possibility for magnification from 5to 300,000×, 3-nm resolution, and acceleration potential from 0 to 30 KV. Through magnifications from 2000 to 5000×, surface details were determined inherent to the material synthesis process through magnetron sputtering, in addition to cell growth and morphology. With EDS the elemental chemical composition was determined, discretely detecting the atomic percentage of elements present in the coatings and substrate. For count calculations and cell population, micrographs were carried out on substrates and layers where initially fibroblast cells from series L929were manually deposited for 72 h of cell growth at 37° C.; the magnifications used were 50 and 500×. Given that these were non-conducting biological samples, they were subjected to metallization process (evaporation of a nanometric layer of gold, generating electric conduction).

Corrosion Resistance

Potentiodynamic curves were analyzed, using the potentiostat-galvanostat system for Ti, TiN, TiZr, TiN/Ti, and TiN/Ti/TiZr thin-film coatings deposited on 316L biocompatible substrate using Potenciostat/Galvavanostat equipment (model 273 A EG&E PRINCETON APPLIED RESEARCH) with cell (model k47 Corrosion Cell System EG&E INSTRUMEN-PRINCETON APPLIED RESEARCH). Reference electrode Hg/KCI was used and platinum as counterelectrode to analyze the thin-film coatings; using a potentiodynamic scan of 1 mV/s. Coating behavior was observed by using two electrolytic solutions, brine (3.5%p/p NaCI) and simulation of blood fluid (Hank's solution); Hank's electrolyte is an artificial physiological solution with environment rich in chloride and pH 7.4. Hank's balanced saline solution is a standard culture medium used in biomedical research for cellular preservation; it is not toxic, has balanced pH, and its osmolarity is 320 mOsm/Kg. This medium has been studied profoundly, showing that during the first 24 h of storage, the fibroblasts remain vital. Said experiments were conducted at human body temperature (~37° C.), using water bath during the process. The composition and concentration of the blood solution are shown in Table 3.

TABLE 3

Composition and concentration of Hank's physiological solution

| Reagent | Concentration (g/L) |
|---|---|
| NaCl | 8 |
| KCl | 0.4 |
| $NaHCO_3$ | 0.35 |
| $C_6H_{12}O_6$ | 1 |
| $NaH_2PO_4 \cdot H_2O$ | 0.25 |
| $MgCl_2 \cdot 6H_2O$ | 0.19 |
| $Na_2HPO_4 \cdot 2H_2O$ | 0.06 |
| $MgSO_4 \cdot 7H_2O$ | 0.06 |

Biological Experimentation

To evaluate biocompatibility, cellular proliferation, cell count, cytotoxicity, and genotoxicity were determined.

Cell count of fibroblasts was accomplished by using SEM and stereoscopy. Samples were cultured in the form of mouse fibroblast monolayer from cell line L929, making observations after 72 h in controlled 37° C. environment on the cell capacity to grow on the surfaces of the coatings synthesized via magnetron sputtering, through SEM and stereoscopy, determining cellular density in the optical field area.

Cell Proliferation Ttest (Kit XTT Cell Proliferation ROCHE®)

The cells were seeded in 24 of the 96 wells of a 96 well tissue culture plate and were incubated with XTT solution (final concentration 0.3 mg/mL) from 4 to 24 h. After this incubation period, the orange-colored formazan solution is made, which is quantified in spectrophotometically by using an ELISA plate reader. The increased number of living cells yields an increase in the total activity of mitochondrial dehydrogenase in the sample, which permits correlating the response with the amount of formazan formed. This result is used to measure cellular proliferation in response to different factors, like cytokines and growth factors. Line L929 is seeded in cell culture microplates, in 24 of the 96 wells, with flat bottom and a final volume of 200 mL of fresh culture medium; the culture is kept in a moist atmosphere (37° C., 5% $CO_2$). After the initial incubation period, the medium is removed and the cells are washed with PBS solution three times for 5 min; thereafter, each well is added 50 mL of the mixture of XTT and 100 mL of the growth medium, generating a final XTT concentration of 0.3 mg/mL. The plates are incubated from 24 to 96 h in moist atmosphere (37° C., 5% $CO_2$). Absorption measurements are performed every 24 h using the microplate reader to verify cellular proliferation of L929 fibroblasts stimulated with magnetic field signals and those not treated with the respective growth controls.

Cytotoxicity Test (Kit LDH ROCHE®)

The cells are incubated for 24 h under conditions (37° C., 5% $CO_2$, 90% humidity) to permit their firmly adhering to the matrix. After the incubation time, the growth medium is removed and the cells are washed three times with PBS for 5 min, and growth medium is added. During the test time, the plates are incubated under the same conditions already described. Cytotoxicity determinations are made at 6 and 24 h, using the ELISA plate reader.

Genotoxicity Test (SOS CHROMOTEST™)

Preliminary dilution of the bacteria was carried out and density was verified, then, 100 μL of the diluted bacterial suspension were added in each well of the columns containing material that will be assayed. The microplates were incubated at 37° C. for 2 h and the relative amount of βgalactosidase, produced as a result of this interaction, is measured by adding a chromogenic substrate.

Comparative Results

Table 4 summarizes the surface, mechanical, tribological, and corrosion properties of the multilayered coating of the invention (TiN/Ti/TiZr) compared to thin layers of Ti, TiN/Ti, TiZr, and TiN. Table 5 presents the results of the biological tests of the multilayered coating of the invention (TiN/Ti/TiZr) compared to the 316L stainless steel substrate used as material for surgical substrates.

TABLE 4

Surface, mechanical, tribological, and corrosion properties

| MATERIAL | PROPERTY | RESPONSE |
|---|---|---|
| Ti | Cell count | 233.33% |
|  | Cellular proliferation | High |
|  | Cytotoxicity | −3.3% |
|  | Genotoxicity | Likely |
|  | COF | 0.8 |
|  | Hardness | 6.76 GPa |
|  | Modulus of elasticity | 179.92 GPa |
| TiN | Cell count | 160% |
|  | Cellular proliferation | High |
|  | Cytotoxicity | 1.5% |
|  | Genotoxicity | Likely |
|  | COF | 0.28 |
|  | Hardness | 17.34 GPa |
|  | Modulus of elasticity | 235.47 GPa |
| TiN/Ti | Cell count | 180% |
|  | Cellular proliferation | High |

TABLE 4-continued

Surface, mechanical, tribological, and corrosion properties

| MATERIAL | PROPERTY | RESPONSE |
|---|---|---|
|  | Cytotoxicity | 2.2% |
|  | Genotoxicity | Unlikely |
|  | COF | 0.71 |
|  | Hardness | 6.68 GPa |
|  | Modulus of elasticity | 254.78 GPa |
| TiZr | Cell count | 368.8% |
|  | Cellular proliferation | Medium |
|  | Cytotoxicity | 3.8% |
|  | Genotoxicity | Unlikely |
|  | COF | 0.5 |
|  | Hardness | 7 GPa |
|  | Modulus of elasticity | 177.16 GPa |
| TiN/Ti/TiZr (coating of the invention) | Cell count | 397.7% |
|  | Cellular proliferation | Medium |
|  | Cytotoxicity | 3.9% |
|  | Genotoxicity | Unlikely |
|  | COF | 0.68 |
|  | Hardness | 6 GPa |
|  | Modulus of elasticity | 154.7 GPa |

TABLE 5

Results of biological tests of the invention coating (TiN/Ti/TiZr) against 316L steel

| PROPERTY | TiN/Ti/TiZr | 316L |
|---|---|---|
| Cell count | 397.7% | 100% |
| Cellular density* | $44.8 \times 10^4$ cells/$cm^2$ | $11.2 \times 10^4$ cells/$cm^2$ |
| Cytotoxicity | 3.9% | 2.4% |
| Genotoxicity SOSIP | Unlikely <0 | Likely >0 |
| COF | 0.68 | 0.90 |
| Hardness | 6 GPa | 4.81 GPa |
| Modulus of Elasticity | 154.7 GPa | 222.6 GPa |
| Roughness | 75 nm | 64 nm |
| Wear rate | $71 \times 2\pi \times 10^{-12}$ $mm^3$/Nm | $12 \times 2\pi \times 10^{-12}$ $mm^3$/Nm |
| Corrosion potential NaCl Solution 3.5% | −167 mV | −270 mV |
| Corrosion potential Hank's Solution | −222 mV | −295 mV |

*Line L929 after incubation during 72 hours

Although the present invention has been described through the preferred embodiments, nonlimiting of the invention, it is understood that the modifications and variations that conserve its essential and elemental content are within the scope of the claims included.

BIBLIOGRAPHY

[1] N. Laube, L. Kleinen, J. Bradenahl, A. Meißner, *"Diamond-like—carbon coatings on ureteral stents—a new strategy in reducing formation of crystalline bacterial biofilms"* Der Urologe (132-141) 2006. Germany.

[2] R. Fellenberg *"Biomedical Applications of Plasma Processing"*. Rev. Society of Vacuum Coaters 50 (2007) ISSN 0737-5921 (107-112).

[3] N. Laube, F. Bruckert, B. Major. "Detachment Kinetics of Eukaryote Cells from Biocompatible PVD Coatings". Rev. Society of Vacuum Coaters 50 (2007) ISSN 0737-5921(113-116)

[4] E. De Las Heras, F. Walthera. *"Microestructura y Comportamiento Frente a la Corrosión de un Acero AISI* 316L *Nitrurado por Plasma"* MEMAT 2005, Mar del Plata, Octubre de 2005.

[5] V. Singh, K. Marchev, C. V. Cooper, E. I. Meletis. "*Intensified plasma-assisted nitriding of AISI 316L stainless steel*". Surface and Coatings Technology 2002, Vol 160 pp 249-258.

[6] M. P. Fewell, D. R. G. Mitchell, J. M. Priest, K. T. Short, G. A. Collins. "*The nature of expanded austenite*". Surface and Coatings Technology 2000, Vol 131 pp 300-306.

[7] Rubin Ortega de la Rosa, Claudia Franco, Eduardo Vald, Guillermo de Anda Rodriguez "*Dispersión Asistida por Magnetron en Peliculas de TiN*"Rev. Fac. Ing.—Univ. Tarapac., vol. 13 N 2, 2005, pp. 31-38.

[8] Y. X. Leng, J. Y. Chen, P. Yang, J. Wang, A. S. Zhao, G. J. Wan, H. Sun, N. Huang "*The microstructure and mechanical properties of TiN and TiO2/TiN duplex films synthesized by plasma immersion ion implantation and deposition on artificial heart valve*" Surface & Coatings Technology 201 (2006) 1012-1016.

[9] D. M. Devia, J. Restrepo, A. Ruden, J. González, F. Sequeda, P. J. Arango "*The Tribological Characteristics of TiN, TiC, TiC/TiN Films Prepared by Reactive Pulsed Arc Evaporation Technique*" Rev. Society of Vacuum Coaters 2009 (32-36) ISSN 0737-5921.

[10] Patent: Ajai Kumar "*Diamond-Like Carbon Coated Dental Instrument*" Apr. 2, 2002. 190 U.S. Pat. No. 6,364,662B1. USA.

[11] A. Devia, V. Benavides, E. Restrepo, D. F. Arias, R. Ospina. Vacuum 81 (2006) 378-384.

[12] Alfonso Devia Cubillos, Elisabeth Restrepo Parra, Belarmino Segura Giraldo, Yulieth Cristina Arango, Diego Fernando Arias Mateus. "Surface & Coatings Technology 190 (2005) 83-89.

[13] D. F. Arias, Y.C. Arango, A. Devia. Applied Surface Science 252 (2005) 1175-1181.

[14] D. Devia, R. Ospina, V. Benavides, E. Restrepo, A. Devia. Vacuum 78 (2005) 67-71

[15] Chiung-Fang Huanga, Hsin-Chung Chenga, Chung-Ming Liuc, Chang-Chih Chena, E, Keng-Liang Oua,f, "*Microstructure and phase transition of biocompatible titanium oxide film on titanium by plasma discharging*" Journal of Alloys and Compounds 476 (2009) 683-688.

[16] Faghihi, S.; Azari, F.; Li, H.; Bateni, M. R.; Szpunar, J. A.; Vali, H.; Tabrizian, M. "*The significance of crystallographic texture of titanium alloy substrates on pre-osteoblast responses*". Biomaterials 2006, 27, 3532-3539.

[17] Sun, Z. L.; Wataha, J. C.; Hanks, C. T. "*Effects of metal ions on osteoblast-like cell metabolism and differentiation*". J. Biomed. Mater. Res. 1997, 34, 29-37.

[18] Kalbacova, M.; Roessler, S.; Hempel, U.; Tsaryk, R.; Peters, K.; Scharnweber, D.; Kirkpatrick, J. C.; Dieter, P "*The effect of electrochemically simulated titanium cathodic corrosion products on ROS production and metabolic activity of osteoblasts and monocytes/macrophages*". Biomaterials 2007, 28, 3263-3272.

[19] Tamaki. Y.; Sasaki, K.; Sasaki, A.; Takakubo, Y.; Hasegawa, H.; Ogino, T.; Konttinen, Y.T.; Salo, J.; Takagi, M. "*Enhanced osteolytic potential of monocytes/macrophages derived from bone marrow after particle stimulation*". J. Biomed. Mater. Res. B 2008, 84, 191-204.

[20] Clohisy, J. C.; Hirayama, T.; Frazier, E.; Han, S. K.; Abu-Amer, Y. NF "*Signalling blockade abolishes implant particle-induced osteoclastogenesis*". J. Orthop. Res. 2004, 22, 13-20.

[21] V. Singh, K. Marchev, C. V. Cooper, E. I. Meletis. "*Intensified plasma-assisted nitriding of AISI 316L stainless steel*". Surface and Coatings Technology 2002, Vol 160 pp 249-258.

[22] Zhendong Hong, Lan Luan, Se-Bum Paik, Bin Deng, Donald E. Ellis "*Crystalline hydroxyapatite thin films produced at room temperature an opposing radio frequency magnetron sputtering approach*" Thin Solid Films 515 (2007) 6773-6780.

[23] S. Hontsu, T. Matsumoto, J. Ishii , M. Nakamori , H. Tabata, T. Kawai "*Electrical properties of hydroxyapatite thin films grown by pulsed laser deposition*" Thin Solid Films 295 (1997) 214-217.

[24] M. Braic, M. Balaceanu, V. Braic, A. Vladescu, T, G. Pavelescu, M. Albulescu. "*Synthesis and characterization of TiN, TiAlN and TiN/TiAlN biocompatible coatings*" Surface & Coatings Technology 200 (2005) 1014-1017.

[25] J. S. Bull "*Tribology of carbon coatings: DLC*" Diamond and related Materials 4(1995)827-836.

[26] M. Sedlaček, B. Podgornik, J. Vižintin "*Tribological properties of DLC coatings and comparison with test results: Development of a database*" Materials Characterization 59 (2008)151-161.

The invention claimed is:

1. A process to manufacture a thin-film multilayered coating for the treatment of biomedical substrates, comprising:
    polishing the substrate surface to a granulometry of between 700 and 2500 to generate a mirror surface finish;
    washing the substrate with acetone in ultrasound for 10 to 20 min;
    submerging the substrate in a PVD-DC magnetron sputtering reactor at a temperature of between 20 and 25° C., vacuum of 5.1×10-6 torr, and 50 to 60% relative humidity;
    depositing a TiN coating layer with thickness of between 550 and 590 nm from a Ti precursor target (99.99%) at a pressure of 2 to 4 mtorr, argon flow between 8 and 12 sccm, nitrogen flow between 0.1 and 0.2 sccm, precursor target potential between 80 and 120 W, polarization voltage from −50 to −120 V, and interelectrode distance between 8 and 12 cm;
    depositing the Ti coating layer with thickness between 550 and 590 nm from a Ti precursor target (99.99%) at a pressure from 2 to 4 mtorr, argon flow between 8 and 12 sccm, precursor target potential between 80 and 120 W, polarization voltage from −50 to −120 V, and interelectrode distance between 8 and 12 cm; and
    depositing the TiZr coating layer with thickness between 550 and 590 rim from a TiZr precursor target (30-70%) at a pressure from 2 ; to 4 mtorr, argon flow between 8 and 12 sccm, precursor target potential between 60 and 100 W, polarization voltage from −50 to −120 V, and interelectrode distance between 8 and 12 cm.

2. A coated biomedical substrate, comprising:
    a multilayered thin-film coat comprising a TiN coating layer having a thickness of between 550 and 590 nm over the substrate; an intermediate layer of Ti having a thickness of between 550 and 590 nm; and
    an external TiZr layer having a thickness between 550 and 590 nm.

3. A surgical implant comprising the coated biomedical substrate of claim 2, wherein the substrate is selected from the group consisting of 316L stainless steel, Co—Cr alloy, and Ti alloy.

* * * * *